US008137560B2

(12) United States Patent
Husbyn

(10) Patent No.: US 8,137,560 B2
(45) Date of Patent: Mar. 20, 2012

(54) SEPARATION PROCESS

(75) Inventor: Mette Husbyn, Oslo (NO)

(73) Assignee: GE Healthcare Limited, Little Chalfont (GB)

( * ) Notice: Subject to any disclaimer, the term of this patent is extended or adjusted under 35 U.S.C. 154(b) by 206 days.

(21) Appl. No.: 12/527,057

(22) PCT Filed: Mar. 7, 2008

(86) PCT No.: PCT/GB2008/000777
§ 371 (c)(1),
(2), (4) Date: Aug. 13, 2009

(87) PCT Pub. No.: WO2008/110757
PCT Pub. Date: Sep. 18, 2008

(65) Prior Publication Data
US 2010/0105888 A1  Apr. 29, 2010

Related U.S. Application Data

(60) Provisional application No. 60/893,892, filed on Mar. 9, 2007.

(51) Int. Cl.
*B01D 15/08* (2006.01)
(52) U.S. Cl. ............ 210/635; 210/656; 210/198.2; 210/502.1; 424/1.89; 536/28.54
(58) Field of Classification Search .......... 210/635, 210/656, 198.2, 502.1; 424/1.89; 536/28.54
See application file for complete search history.

(56) References Cited

U.S. PATENT DOCUMENTS

| 7,119,145 | B2 * | 10/2006 | Dixon et al. | 525/64 |
| 7,807,821 | B1 * | 10/2010 | Sekine et al. | 536/25.31 |
| 2008/0182284 | A1 * | 7/2008 | Haugland et al. | 435/21 |

FOREIGN PATENT DOCUMENTS

| WO | WO 03/064478 | * | 8/2003 |
| WO | 2005025519 | | 3/2005 |
| WO | 2006133732 | | 12/2006 |
| WO | WO 2006/133732 | * | 12/2006 |

OTHER PUBLICATIONS

Kellie J. Williams, et.al. "Critical elements of oligosaccharide acceptor substrates for the pateurella multocida hyaluronan synthase" J. Biol. Chem., vol. 281, No. 9, 2006 pp. 5391-5397.
Bart Baijens: Rijksinstitute Voor Integraal Zoetwaterbeheer en Afvalwaterbehandeling/RIZA, Jan. 2004, Lelystad Annex 1 (Bijlage 1) Oasis HLB and Strata X—both surface modified styrene-divinylbenzene polymers.
Blocher, et.al. "Synthesis and labeling of 5'-O-(4,4'-dimethoxytrityl)-2,3'-anhydrothymidine for [18F]FLT preparation" Journal of Radioanalytical and Nuclear Chemistry, vol. 251, vo. 1 (2002) pp. 55-58.
Machulla, et.al. "Simplified labeling approach for synthesizing 3'-deoxy-3'-[18F]fluorothymidine ([18F]FLT)" Journal of Radioanalytical and Nuclear Chemistry, vol. 243, No. 3, 2000, pp. 843-846.

* cited by examiner

*Primary Examiner* — Ernest G Therkorn

(57) ABSTRACT

The present invention relates to a process for separating a target radiolabelled compound from an impurity, apparatus for performing such a process and a removable cassette for use in such apparatus. Also provided are methods for using the target radiolabelled compound obtained by a method comprising the separating process of the invention.

8 Claims, 2 Drawing Sheets

SEPARATION PROCESS

This application is a filing under 35 U.S.C. 371 of international application number PCT/GB2008/000777, filed Mar. 7, 2008, which claims priority to application number 60/893,892 filed Mar. 9, 2007, in The United States the entire disclosure of which is hereby incorporated by reference.

SUMMARY OF THE INVENTION

The present invention relates to a process for separating a target radiolabelled compound from an impurity, apparatus for performing such a process and a removable cassette for use in such apparatus. Also provided are methods for using the target radiolabelled compound obtained by a method comprising the separating process of the invention.

BACKGROUND OF THE INVENTION

Radiolabelled compounds have uses in medical imaging and, in the case of $^{18}$F radiolabelled compounds, in Positron Emission Tomography (PET).

One family of radiolabelled compounds of particular, current interest are radiolabelled thymidines and, in particular, 3'-deoxy-3'-[$^{18}$F] fluorothymidine ($^{18}$FLT) for PET imaging especially in the field of oncology.

$^{18}$FLT may be synthesized from 5'-O-(4',4'-dimethoxytrityl) thymidine by nucleophilic substitution (with inversion of stereo chemistry) at the 3' position using $^{18}$F as illustrated in scheme 1.

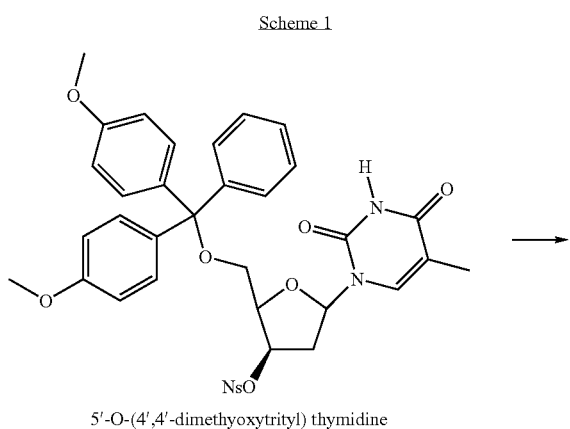

5'-O-(4',4'-dimethyoxytrityl) thymidine

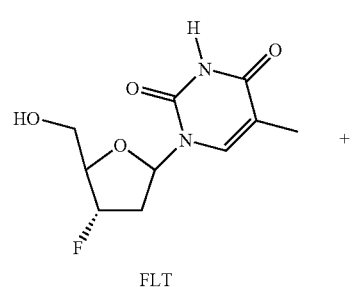

FLT

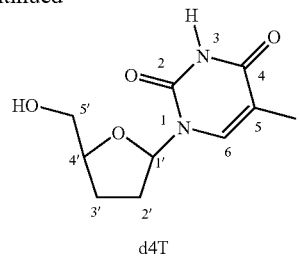

d4T

During this fluorination procedure, the elimination product d4T is often formed in high yield owing to competition between OH$^-$ and $^{18}$F$^-$ and is therefore the main impurity in this reaction. d4T tends to be formed at a much higher rate than $^{18}$FLT and may be present in a d4T:$^{18}$FLT ratio of 100-10000:1. Separation of $^{18}$FLT and d4T may be problematic.

High performance liquid chromatographic separation of the two compounds may be achieved using different stationary phases, however HPLC is costly and complex and not a preferred purification method in a clinical environment such as a hospital.

HPLC methods can also be time consuming which is a particular problem with the use of radionuclides with short half lives ($^{18}$F has a half-life of about 110 minutes). Another serious problem is that HPLC does not lend itself to use with commercially available synthesis modules which simplify the preparation and purification of radiolabelled compounds.

WO 2005/025519 describes a method and apparatus for the automated synthesis of $^{18}$FLT in which a separation procedure is performed using a Sep-Pak® C-18 solid phase extraction (SPE) column.

WO 2006/133732 also describes a method for the manufacture of [$^{18}$F]-FLT in which a separation is performed using an Oasis® HLB SPE column.

Unfortunately, the SPE methods previously described for use in the manufacture of [$^{18}$F]-FLT do not result in good enough separation and so are not always suitable for clinical use.

The present invention aims to address the problems mentioned above by providing a separation process which is relatively simple, less costly than HPLC, results in excellent separation and lends itself to use, especially, in a clinical environment.

DETAILED DESCRIPTION OF THE INVENTION

The present invention accordingly provides, in a first aspect, a process for separating a target radiolabelled compound and one or more impurities, the process comprising,
  providing a mixture comprising the target radiolabelled compound and one or more impurities;
  passing the mixture through a solid phase extraction column to adsorb the target radiolabelled compound and adsorb said one or more impurities, said solid phase extraction column containing a polymeric surface modified sorbent;
  eluting said one or more impurities using a first elution solution; and,
  eluting the target radiolabelled compound using a second elution solution.

An "impurity" is understood in its conventional sense, i.e. any impurity originating from the chemical or radiochemical process.

The process according to the first aspect of the invention is advantageous because it allows relatively simple, cost-effective robust and rapid separation of the target radiolabelled compound from one or more impurities. It is also advantageous because of the good separation possible since both the target radiolabelled compound and an impurity are adsorbed on the solid phase extraction column with different affinities. Separate elutions of an impurity and the target using the first and second elution solutions enable a fine-tuned control of the separation process.

Preferably, the target radiolabelled compound is a radiolabelled thymidine or thymidine derivative. More preferably, the target radiolabelled compound is radiolabelled 3'-deoxy-3'-thymidine, or a derivative thereof.

Radiolabelled thymidine or derivatives thereof are advantageous because they are useful radiolabelled compounds in PET and Single Photon Emission Computed Tomography (SPECT), finding use in various areas including oncology.

The target radiolabelled compounds may be radiolabelled with various radionuclides. Particularly suitable for the present invention are gamma-emitting radiohalogens suitable for SPECT imaging, or positron-emitters suitable for PET imaging. Examples of gamma-emitting radiohalogens include $^{123}$I, $^{131}$I and $^{77}$Br, $^{123}$I being preferred. For PET imaging, suitable radionuclides include $^{11}$C, $^{18}$F, $^{75}$Br, $^{76}$Br and $^{124}$I, with Br, $^{11}$C and $^{18}$F being preferred, and $^{18}$F most preferred. Methods to obtain such radiolabelled compounds are described in the Handbook of Radiopharmaceuticals (Wiley; 2003: Welch and Redvanly, Eds.).

A preferred target radiolabelled compound of the invention is $^{18}$F-labelled FLT (3'-deoxy-3'-[$^{18}$F] fluorothymidine). $^{18}$F-labelled FLT may be obtained by the method described by Hamacher et al (1986 J. Nuc. Med.; 27; 235).

A process for producing FLT may result in impurities because of side reactions. Impurities may be, in particular, a thymidine or a thymidine derivative. One impurity of particular concern is 2',3'-didehydro-3'-deoxythymidine.

The process of the invention in the first aspect is conducted wherein the solid phase extraction column contains a polymeric surface modified sorbent. Surface modified sorbents are sorbents which comprise a support (which may be, for example, silica or a polymer) which is modified by introducing functional chemical groups on the surface (usually including the internal surfaces of any pores) of the particles of the sorbent. A wide variety of possible chemical groups may be used to surface modify sorbents, depending, to a certain extent, on the nature of the support. Polymeric surface modified sorbents are particularly advantageous because the supporting sorbent can be selected from a large number of polymers with a large variety of properties, in particular surface area, porosity and particle size, thereby providing different selectivities within one sorbent (e.g. hydrophobicity, hydrophilicity, pi-pi interactions) and excellent stability within a large pH range (1-14).

In the case of a polymeric surface modified sorbent, preferably the polymer surface modified sorbent comprises a surface modified poly(styrene divinyl benzene). This is advantageous because poly(styrene divinyl benzene) is available in a range of particle sizes, surface areas and porosities and is relatively readily surface modified by the introduction of various chemical groups. One way in which poly(styrene divinyl benzene) may be surface modified is described in WO-A-03/064478 and involves free radical-initiated surface graft modification of residual free vinyl groups on the surface of the base polymer.

A preferred polymeric surface modified polymer sorbent is surface modified with a pyrrolidone or piperidone derivative, more preferably a 2-pyrrolidone or 2-piperidone derivative. This is advantageous because such surface modified polymeric sorbents provide excellent separation of target radiolabelled compounds and impurities using two elution solutions, in particular for radiolabelled thymidines or thymidine derivatives.

The solid phase extraction column may generally be of any appropriate size taking into account the volume of mixture to be separated. However, in a clinical environment the solid phase extraction column will usually have an effective volume in the range of 1-10 ml ($cm^3$), usually 2-8 $cm^3$ or 3-6 $cm^3$.

The solid phase extraction column will normally be loaded with sufficient polymeric surface modified sorbent to ensure there is good separation of the target radiolabelled compound and the impurity. Generally, the solid phase extraction column will be loaded with between 10 and 200 mg per $cm^3$ of the surface modified sorbent based on the effective volume of the solid phase extraction column. Preferably, the solid phase extraction column will be loaded with 20 mg/$cm^3$ to 145 mg/$cm^3$, more preferably 50 to 100 mg/$cm^3$ and most preferably 50 to about 90 mg/$cm^3$. Typical, preferred, loadings of the solid phase extraction column would be 60 mg for a 3 $cm^3$ column (equivalent to 20 mg/$cm^3$) to 850 mg for a 6 $cm^3$ column (equivalent to about 142 mg/$cm^3$).

Sorbent quantity also influences the quantity of sample loaded onto the column. This will in general be 5-10% of the sorbent quantity.

Preferably, the first and/or second elution solutions comprise one or more solvents selected from acetonitrile, alkanol and water. The preferred alkanol comprises ethanol.

Generally, the first and the second elution solutions each will comprise water and either acetonitrile or ethanol, the two systems differing in their proportion of acetonitrile or ethanol in water. This is advantageous because it simplifies the supply of the elution solutions to the column in order to elute either the impurity or the target radiolabelled compounds, since elution of either the impurity or the target radiolabelled compound will depend upon varying the proportion of either acetonitrile or ethanol in water. It is also advantageous because it enables fine control of the separation process by making fine adjustments to the ratio of water and either acetonitrile or ethanol. Typically, higher proportions of acetonitrile or ethanol are required in order to elute the target compound as opposed to the impurity. Typical proportions of acetonitrile or ethanol in water are 3 to 5% (for elution of the impurity) up to 12 to 20% (for elution of the target compound).

Ethanol is the preferable solvent as the resultant solution can be directly injected in to the patient (when diluted to max 7% v/v). There is no need for an additional solvent exchange step before injection.

One of the benefits of the present invention is that relatively low pressures can be used in order to achieve separation using the solid phase extraction column. Typical pressures are around ambient pressure, although higher pressures may be used if necessary, e.g. up to around 800 kPa [8 bar].

Generally, in the first aspect of the invention, eluting comprises passing the first or second elution solution through the solid phase extraction column at a flow rate of 0.5-20 ml/min$^-$$_1$. More preferably, the flow rates of 0.5 to 15 ml/min, 1.0 to 5.0 ml/min and, most preferably, 1.0 to 3.0 ml/min may be used. Lower flow rates generally result in better separation.

Prior to using the solid phase extraction column for the process of the present invention, it needs to be "conditioned". This simply involves an initial washing with an organic solvent, which will typically be the organic solvent to be used in the rest of the process.

The process of the present invention may include a number of further steps including a drying step by which the sorbent of the solid phase extraction column is dried, possibly a drying step after loading of the sample to be separated on the column but before elution. Further steps that may be included in the separation process are a flushing step or washing step to wash the solid phase extraction column generally at any appropriate stage in the procedure.

The separation process of the present invention is very advantageous because it allows for efficient separation of the target radiolabelled compound from the impurity. Typically, eluting the impurity using the first elution solution produces one or more fractions containing in total less than 10% of the target radiolabelled compound, more preferably 5% or less of the target radiolabelled compound, most preferably 2% or less of the target radiolabelled compound.

Furthermore, the present process is advantageous because, generally, eluting the target radiolabelled compound using the second elution solution produces one or more fractions having a purity in the target compound of greater than 90%. More preferably, the second elution solution produces one or more fractions having a purity in the target compound of greater than 94, 95 or 96%.

In a second aspect, the present invention provides a method for the synthesis of a target radiolabelled compound which comprises the process for separating of the first aspect of the invention.

Preferred and most preferred embodiments of the target radiolabelled compound and of the process for separating are as provided for the first aspect of the invention.

In an especially preferred embodiment, the method for the synthesis of a target radiolabelled compound is automated. For example, U.S. Pat. No. B-6,172,207 describes a method for synthesising [$^{18}$F]-FDG using multiple stopcock manifolds and disposable sterile syringes. This corresponds to the commercially-available TRACERlab MX$_{FDG}$® apparatus, marketed by GE Healthcare.

The present invention provides, in a third aspect, an apparatus for the automated synthesis of a target radiolabelled compound, wherein said synthesis comprises separating the target radiolabelled compound and at least one impurity, the apparatus comprising:
  a solid phase extraction column for adsorbing the target radiolabelled compound and adsorbing said at least one impurity, said solid phase extraction column containing a polymeric surface modified sorbent;
  means for supplying a first elution solution to the column to elute the impurity; and,
  means for supplying a second elution solution to the column to elute the target radiolabelled compound.

The features of the third aspect of the invention are generally the same (with appropriate modification) as those relevant features relating to the first aspect of the invention.

In a fourth aspect of the invention, the present invention provides a removable cassette for use with an apparatus for the automated synthesis of a target radiolabelled compound, the cassette comprising a solid phase extraction column containing a polymeric surface modified sorbent. Such removable cassettes are designed to be plugged into a suitably adapted automated synthesiser apparatus, such as TRACERlab®. Removable cassettes are very advantageous because they improve the cost-effectiveness, efficiency and speed of the separation. They also ensure that set-up time is minimised and set-up is simplified, both of great importance, especially in a clinical environment (for example, a hospital). The removable cassette may generally have the features as described in relation to the previous aspects of the invention, with appropriate modifications.

The removable cassette may contain, apart from the solid-phase extraction column, a vessel containing precursor compound, a column to remove any unwanted radioactive ion, and an appropriate vessel connected so as to allow the reaction mixture to be evaporated and allow the product to be formulated as required. The reagents and solvents and other consumables required for the synthesis may also be included together with a compact disc carrying the software which allows the automated synthesiser to be operated in a way so as to meet the customers' requirements for radioactive concentration, volumes, time of delivery, etc. Conveniently, all components of the removable cassette are disposable to minimise the possibility of contamination between runs and may be sterile and quality assured.

The removable cassette for the automated synthesis of a target radiolabelled compound may comprise:
  (i) a vessel containing a precursor compound;
  (ii) means for eluting the vessel with a source of the desired radionuclide;
  (iii) an ion-exchange cartridge for removal of excess radionuclide;
  (iv) a cartridge for deprotection of the resultant target radiolabelled compound; and,
  (v) a cartridge for separating the target radiolabelled compound and one or more impurities, said cartridge comprising a solid phase extraction column containing a polymeric surface modified sorbent.

In a fifth aspect of the present invention, the invention provides a method of generating an image comprising:
  (i) providing a subject to whom a detectable quantity of a target radiolabelled compound has been administered, said compound obtained by a method comprising the process of the first aspect of the invention;
  (ii) allowing the target radiolabelled compound to biodistribute in said subject;
  (iii) detecting signals emitted by said target radiolabelled compound by an in vivo imaging method; and,
  (iv) generation of an image representative of the location and/or amount of said signals.

The method of the fifth aspect of the invention begins by "providing" a subject to whom a detectable quantity of a target radiolabelled compound has been administered. Since the ultimate purpose of the method is the provision of an image, administration to the subject of said target radiolabelled compound can be understood to be a preliminary step necessary for facilitating generation of said image.

The "subject" of the invention is preferably a mammal, most preferably an intact mammalian body in viva In an especially preferred embodiment, the subject of the invention is a human.

The "detection" step of the method involves the detection of signals emitted by the radionuclide by means of a detector sensitive to said signals, such as SPECT and PET detectors.

The "generation" step of the method of the invention is carried out by a computer which applies a reconstruction algorithm to the acquired signal data to yield a dataset. This dataset is then manipulated to generate images showing areas of interest within the subject.

Preferred and most preferred embodiments of the process of separation and the target radiolabelled compound are as provided for the first aspect of the invention.

In a sixth aspect, the present invention provides a method of diagnosis comprising:

(i) the preliminary step of administering a target radiolabelled compound to a subject, said compound obtained by a method comprising the process of the first aspect of the invention;
(ii) steps (i) to (iv) of the method of generating an image of the fifth aspect of the invention; and,
(iii) evaluating the image generated in step (iv) of said method of generating an image to diagnose a pathological condition.

Preferred and most preferred embodiments of the process of separation and the target radiolabelled compound are as discussed in relation to the first aspect of the invention.

EXPERIMENTAL EXAMPLES

Figure 1:
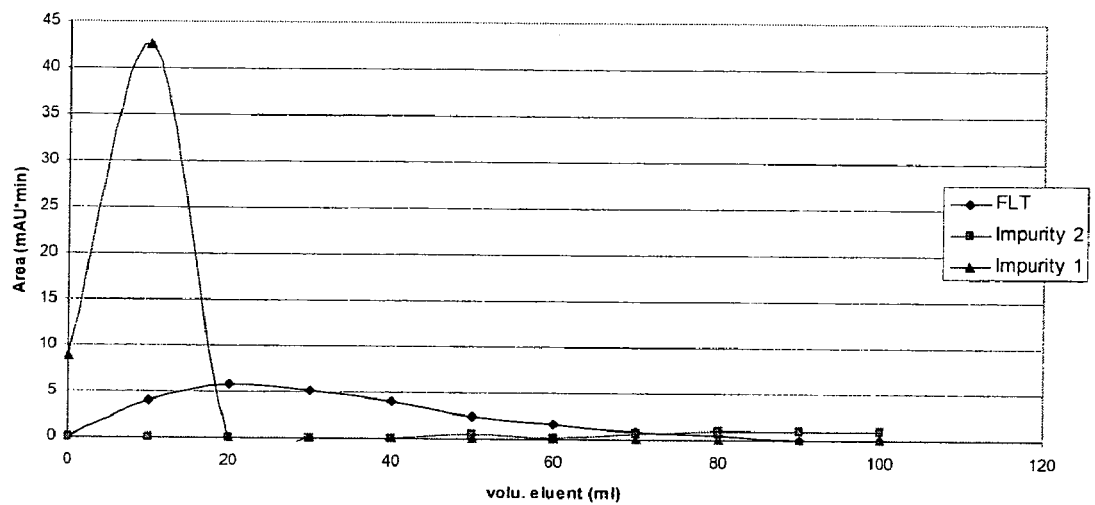
FIG. 1 is a chart showing elution as a function of volume of eluent (5% ethanol in water) of crude FLT using a co-polymerised sorbent (OASIS HLB).

The invention is also illustrated by the following non-limiting examples.

Examples 1 to 3

In Examples 1 to 3, the separation of a model compound $^{19}$FLT and d4T was studied using a solid phase extraction column. $^{19}$FLT is fluorinated with naturally-abundant $^{19}$F instead of the radionuclide $^{18}$F.

The fractions after SPE separation were analysed using HPLC (Luna C18(2) 5 µm column (obtained from Phenomenex), 4.6×250 mm A) 0.1% TFA/H$_2$O, B) 0.1% TFA/MeCN. Isocratic 9% B 15 min flow rate 1 ml/min).

The general procedure was as follows:
1. Column activation: 1×6 ml MeCN
2. Column wash: 1×6 ml H$_2$O
3. Application of sample: d4T:$^{19}$FLT 100:1
4. Impurity elution: e.g. 4×6 ml 2% MeCN
5. Target elution: e.g. 1×6 ml 12% MeCN
6. Final wash: 1×6 ml 100% MeCN or 1. Column activation: 1×6 ml EtOH
2. Column wash: 1×6 ml H$_2$O
3. Application of sample: d4T:$^{19}$FLT 100:1
4. Impurity elution: e.g. 5×6 ml 5% EtOH and e.g. 1×6 ml 8% EtOH
5. Target elution: 1×6 ml 20% EtOH (17 ml injection volume of 7% EtOH)
6. Final wash 100% EtOH The sorbent used was a surface modified poly(styrene divinyl benzene) modified with N-linked 2-piperidone groups and available from Phenomenex under the trade name Strata™ X. Column size in examples 1-3: 6 ml/500 mg sorbent; temperature: ambient; pressure: ambient.

Conditioning of the column was carried out before application of the sample in each case, e.g. for Example 1 an application of 1×6 ml acetonitrile followed by an application of 1×6 ml water.

Example 1

1. Application of Sample
   d4T (6 mg) $^{19}$FLT (0.060 mg) was dissolved in 300 µl water. 270 µl was applied on to the Strata™ X column.
2. Washing of Column
   i) 4×6 ml of 2% acetonitrile was used to wash off d4T. A minute amount of $^{19}$FLT was observed in the final washing fraction. No exact quantification was performed.
3. Elution
   1×6 ml 12% acetonitrile was used to elute $^{19}$FLT, and the HPLC purity was 96%.
4. Control
   The column was washed with 100% acetonitrile and the fraction was analysed by HLPC. Neither d4T nor $^{19}$FLT was detected.

Example 2 d4T (10 mg) was dissolved in H$_2$O (200 µl) and 100 µl of a $^{19}$FLT solution of 1 mg/ml was added. 30 µl was withdrawn for HPLC analysis. The remaining 270 µl was applied on to the column. The column was activated (MeCN) and washed with water. The following procedure was used:

5×6 ml 5% EtOH/H$_2$O

2×6 ml 8% EtOH/H$_2$O

1×6 ml 20% EtOH/H$_2$O

The experiment was successful, showing a purity (in the 20% EtOH fraction) of $^{19}$FLT of 96.5%. There was no detectable breakthrough of $^{19}$FLT in any of the 8% EtOH/H$_2$O fractions.

Example 3 d4T (10 mg) was dissolved in H$_2$O (200 µl). $^{19}$FLT (100 µl of a 1 mg/ml H$_2$O solution) was added. 30 µl was taken out for HPLC analysis. 270 µl was applied on to the Strata™ X (500 mg/6 ml) column. The column was activated with MeCN and washed with H$_2$O prior to the application of sample.

Procedure:

5×6 ml 6% EtOH/H$_2$O

2×6 ml 8% EtOH/H$_2$O

1×6 ml 20% EtOH/H$_2$O

1×6 ml 100% EtOH

Samples were analysed using HPLC.

The 20% EtOH fraction has a purity in $^{19}$FLT of 96.4%. However, fraction 7 also contained some $^{19}$FLT, such that Fractions 7 and 8 combined gave a purity of $^{19}$FLT of 96%.

Example 4

Separation of FLT and impurities using two different sorbents was investigated.

Test 1

Crude $^{18}$FLT (decayed) product obtained from a commercial synthesizer was mixed in each case with 2 mg of $^{19}$FLT to give a total analyte volume of 10 ml. The analyte sample was trapped on a SPE cartridge containing the sorbent Oasis HLB (obtained from Waters Corporation). Oasis HLB is a co-polymerised sorbent with a specific ratio of the monomers N-vinylpyrrolidone and divinylbenzene.

The cartridge was dried and then eluted with 5% ethanol in water at a flow rate of 5 ml/min. 10 ml fractions were collected. The results are illustrated in FIG. 1 and show poor separation of FLT and the two impurities.

Test 2

Figure 2:
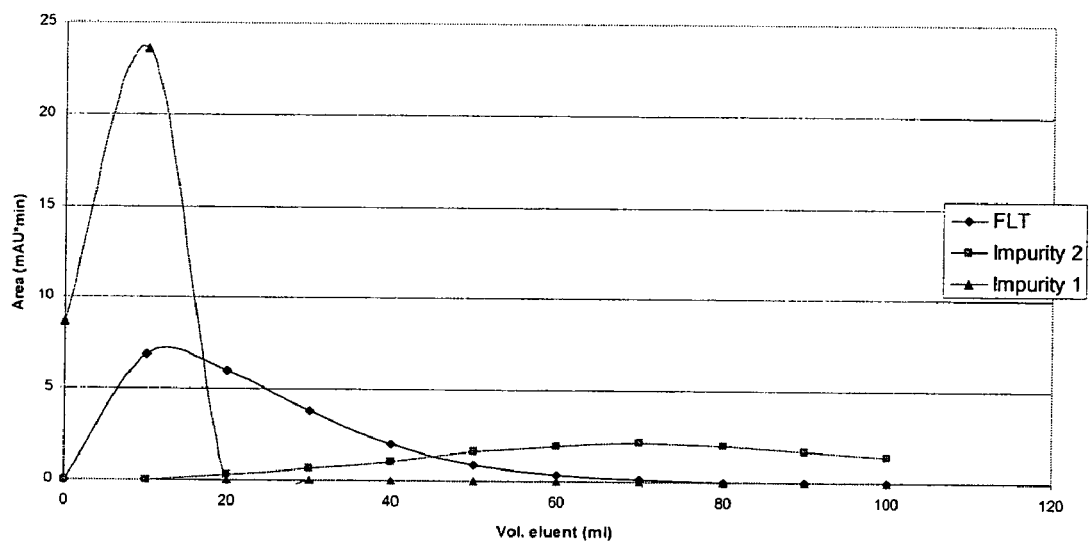
FIG. 2 is a chart showing elution as a function of volume of eluent (7% ethanol in water) of crude FLT using the sorbent of FIG. 1.

Test 1 was repeated, except that 7% ethanol in water was used as the eluent. The results are illustrated in FIG. 2 and also show poor separation.

Test 3

Figure 3:
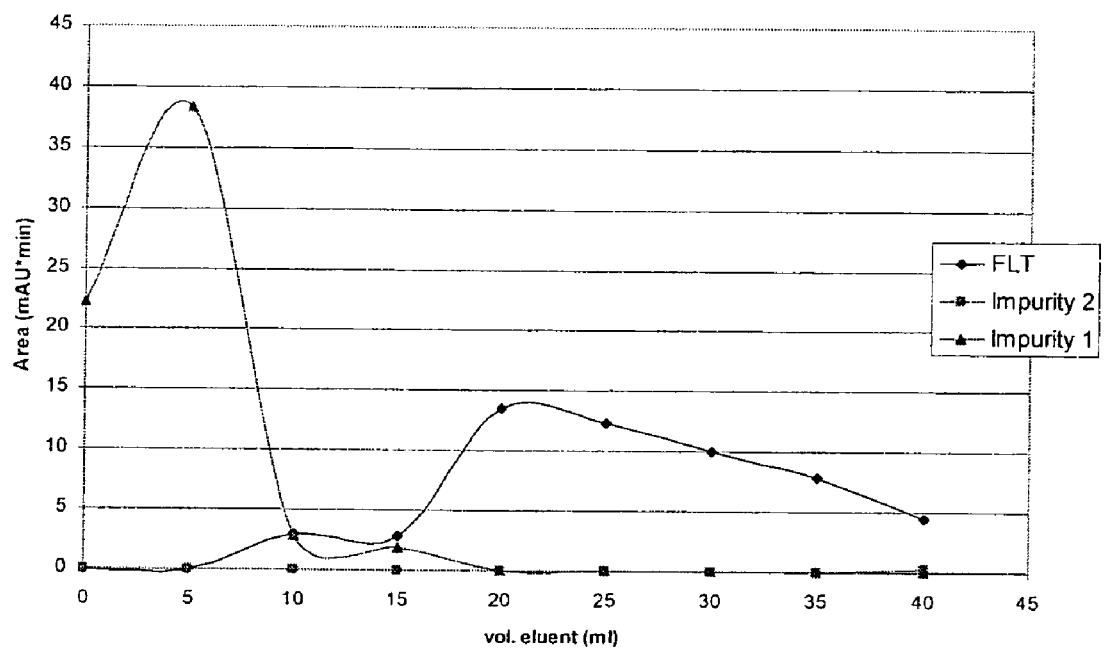
FIG. 3 is a chart showing elution as a function of volume of eluent (7% ethanol in water) of crude FLT using a surface modified sorbent (Strata™ X).

Test 2 was repeated, except that the sorbent used was Strata™ X (obtained from Phenomenex). Strata™ X is a surface modified poly(styrene divinyl benzene) copolymer, surface modified with 2-piperidone. The results are illustrated in FIG. 3 and show good separation.

Example 4 shows that the sorbent and elution solutions are important in separation of FLT and impurities.

What is claimed is:

1. A process for separating a target radiolabelled compound and one or more impurities, wherein the target radiolabelled compound is a radiolabelled thymidine or thymidine derivative, the process comprising, providing a mixture comprising the target radiolabelled compound and one or more impurities;

passing the mixture through a solid phase extraction column to adsorb the target radiolabelled compound and adsorb said one or more impurities, said solid phase extraction column containing poly(styrene divinyl benzene) surface modified with 2-piperidone;

eluting said one or more impurities using a first elution solution; and, eluting the target radiolabelled compound using a second elution solution.

2. A process as claimed in claim 1, wherein the target radiolabelled compound is radiolabelled 3'-deoxy-3'-thymidine, or a derivative thereof.

3. A process as claimed in claim 1, wherein the target radiolabelled compound is radiolabelled with $^{18}$F.

4. A process as claimed in claim 1, wherein the target radiolabelled compound is 3'-deoxy-3'-[$^{18}$F] fluorothymidine.

5. A process as claimed in claim 1, wherein said one or more impurities is a thymidine or a thymidine derivative.

6. A process as claimed in claim 5, wherein the impurity is 2', 3'-didehydro-3'-deoxythymidine.

7. A method for the synthesis of a target radiolabelled compound which comprises the process of claim 1.

8. The method of claim 7 which is automated.

* * * * *